United States Patent [19]

Berg et al.

[11] Patent Number: 4,948,471
[45] Date of Patent: Aug. 14, 1990

[54] SEPARATION OF 4-METHYL-2-PENTANONE FROM FORMIC OR ACETIC ACID BY EXTRACTIVE DISTILLATION WITH SULFOLANE

[75] Inventors: Lloyd Berg, 1314 S. 3rd Ave., Bozeman, Mont. 59715; George Bentu, Bozeman, Mont.

[73] Assignee: Lloyd Berg, Bozeman, Mont.

[21] Appl. No.: 387,814

[22] Filed: Aug. 1, 1989

[51] Int. Cl.$^5$ ............................ B01D 3/40; C07C 51/44
[52] U.S. Cl. ........................................... 203/51; 203/57; 203/58; 203/60; 203/61; 203/62; 203/63; 203/64; 562/608; 562/609; 568/410
[58] Field of Search ................. 203/58, 51, 57, 62, 203/63, 60, 61; 568/410; 562/608, 609

[56] References Cited

U.S. PATENT DOCUMENTS

| | | | |
|---|---|---|---|
| 2,570,205 | 10/1951 | Carlson et al. | 203/58 |
| 2,586,929 | 2/1952 | Fleming et al. | 568/410 |
| 3,013,954 | 12/1961 | Pacoud et al. | 203/62 |
| 3,265,592 | 8/1966 | Van Der Weel | 568/410 |
| 3,309,407 | 3/1967 | Carpenter et al. | 568/410 |
| 4,735,690 | 4/1988 | Berg et al. | 203/58 |
| 4,793,901 | 12/1988 | Berg et al. | 203/51 |
| 4,840,707 | 6/1989 | Berg et al. | 203/51 |
| 4,859,285 | 8/1989 | Berg et al. | 203/51 |

*Primary Examiner*—Wilbur Bascomb

[57] ABSTRACT

4-Methyl-2-pentanone cannot be easily separated from formic acid or acetic acid by distillation because of the closeness of their boiling points. 4-Methyl-2-pentanone can be readily removed from formic acid or acetic acid by extractive distillation. Typical effective agents are sulfolane; sulfolane and heptanoic acid; sulfolane, azelaic acid and ethylene glycol diacetate.

4 Claims, No Drawings

SEPARATION OF 4-METHYL-2-PENTANONE FROM FORMIC OR ACETIC ACID BY EXTRACTIVE DISTILLATION WITH SULFOLANE

FIELD OF THE INVENTION

This invention relates to a method for separating 4-methyl-2-pentanone from formic acid or acetic acid with sulfolane as the agent in extractive distillation.

DESCRIPTION OF PRIOR ART

Extractive distillation is the method of separating close boiling compounds or azeotropes by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during the extractive distillation and thus make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil twenty Celcius degrees or more higher than the lowest boiling component.

At the bottom of a continuous column, the less volatile component of the close boiling mixtures and the extractive agent are continuously removed from the column. The usual methods of separation of these two components are the use of another rectification column, cooling and phase separation or solvent extraction.

4-Methyl-2-pentanone, B.P.=117° C. and formic acid, B.P.=101° C. possess an average relative volatility of about 1.3 and boil so close together that they are difficult to separate by conventional rectification. Extractive distillation would be an attractive method of effecting the separation of 4-methyl-2-pentanone from formic acid if agents can be found that (1) will enhance the relative volatility of 4-methyl-2-pentanone to formic acid and (2) are easy to recover from the formic acid, that is, form no azeotrope with formic acid and boil sufficiently above formic acid to make separation by rectification possible with only a few theoretical plates.

Acetic acid and 4-methyl-2-pentanone boil only 2.5 Celsius degrees apart and thus have a relative volatility of only 1.06. Table 1 shows the boiling point relationship for these two compounds at 640 mm.HG pressure. From Table 1, it can be seen that in concentrations of 4-methyl-2-pentanone below 77 percent, the boiling point changes only 0.5° C. and further separation by rectification becomes virtually impossible. Although the overall relative volatility is 1.06, in this region it is almost 1.0, just about as difficult to separate as an azeotrope.

TABLE 1

Boiling Points of 4-Methyl-2-pentanone - Acetic Acid Mixtures at 640 mm. Hg.

| % 4-Methyl-2-pentanone | % Acetic Acid | Boiling Point, °C. |
|---|---|---|
| 100 | 0 | 109 |
| 90 | 10 | 110 |
| 77 | 23 | 111 |
| 50 | 50 | 111.2 |
| 40 | 60 | 111.2 |
| 33 | 67 | 111.3 |
| 23 | 77 | 111.4 |
| 10 | 90 | 111.4 |
| 0 | 100 | 111.5 |

Extractive distillation would be an attractive method of effecting the separation of 4-methyl-2-pentanone from formic and acetic acid if agents can be found that (1) increase the relative volatility of 4-methyl-2-pentanone to the acids and (2) are easy to recover from the acids, that is, form no azeotrope with the acids and boil sufficiently above the acids to make separation by rectification possible with only a few theoretical plates.

Extractive distillation typically requires the addition of an equal amount to twice as much extractive agent as the acid-water on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required if the separation is done by azeotropic distillation. Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is desirable that the extractive agent be miscible with formic acid otherwise it will form a two-phase azeotrope with the formic acid in the recovery column and some other method of separation will have to be employed.

OBJECTIVE OF THE INVENTION

The object of this invention is to provide a process or method of extractive distillation that will enhance the relative volatility of 4-methyl-2-pentanone from formic or acetic acid in their separation in a rectification column. It is a further object of this invention to identify organic compounds which are stable, can be separated from acetic acid by rectification with relatively few plates and can be recycled to the extractive distillation column and reused with little decomposition.

SUMMARY OF THE INVENTION

The objects of the invention are provided by a process for separating 4-methyl-2-pentanone from formic acid or acetic acid which entails the use of sulfolane, either alone or admixed with high boiling organic compounds as the agent in extractive distillation.

DETAILED DESCRIPTION OF THE INVENTION

We have discovered that sulfolane, either alone or admixed with other high boiling organic compounds, will effectively increase the relative volatility of 4-methyl-2-pentanone to formic acid or acetic acid and permit the separation of 4-methyl-2-pentanone from formic acid or acetic acid by rectification when employed as the agent in extractive distillation. Table 2 lists sulfolane and its mixtures and the approximate proportions that we have found to be effective with formic acid. The data in Table 2 was obtained in a vapor-liquid equilibrium still. In each case the starting material was a 50–50 wt.% mixture of 4-methyl-2-pentanone and formic acid. The ratios are the parts by weight of extractive agent used per part of 4-methyl-2-pentanone-formic acid mixture. The relative volatilities are listed for each of the two ratios employed. The compounds which are effective when used in mixtures with sulfolane are adipic acid, acetyl salicylic acid, azelaic acid, benzoic acid, p-tert. butyl benzoic acid, cinnamic acid, decanoic acid, glutaric acid, heptanoic acid, hexanoic acid, itaconic acid, malic acid, neodecanoic acid, m-nitrobenzoic acid, octanoic acid, pelargonic acid, salicylic acid, sebacic acid, thiosalicylic acid, m-toluic acid, ethylene glycol diacetate, benzyl ether, dipropylene glycol dibenzoate, 2-methoxyethyl ether, acetophenone, methyl isoamyl ketone, glycerol triacetate, ethylene glycol butyl ether acetate, isophorone, cyclopentanone, nitrobenzene and diethyl maleate.

The two relative volatilities shown in Table 2 correspond to the two different ratios investigated. For example, in Table 2, two parts of sulfolane mixed with one part of 4-methyl-2-pentanone-formic acid mixture give a relative volatility of 2.9, 12/5 parts of sulfolane give 1.9. One half part of sulfolane mixed with one half part of itaconic acid with one part of the 4-methyl-2-pentanone-formic acid mixture give a relative volatility of 3.6, 3/5 parts of sulfolane plus 3/5 parts of itaconic acid give 4.6.

TABLE 2

Effective Extractive Distillation Agents For 4-methyl-2-pentanone From Formic Acid

| Compounds | Ratios | | Relative Volatilities | |
|---|---|---|---|---|
| Sulfolane | 2 | 12/5 | 2.9 | 1.9 |
| Sulfolane, Adipic acid | (½)[2] | (3/5)[2] | 4.0 | 2.6 |
| Sulfolane, Acetyl salicylic acid | " | " | 1.4 | 1.8 |
| Sulfolane, Azelaic acid | " | " | 1.3 | 1.5 |
| Sulfolane, Benzoic acid | " | " | 1.2 | 2.0 |
| Sulfolane, p-tert. Butyl benzoic acid | " | " | 2.4 | — |
| Sulfolane, Cinnamic acid | " | " | 2.1 | 1.2 |
| Sulfolane, Decanoic acid | " | " | 1.2 | 1.2 |
| Sulfolane, Glutaric acid | " | " | 2.2 | 3.1 |
| Sulfolane, Heptanoic acid | " | " | 1.6 | 1.6 |
| Sulfolane, Hexanoic acid | " | " | 1.3 | 1.2 |
| Sulfolane, Itaconic acid | " | " | 3.6 | 4.6 |
| Sulfolane, Malic acid | " | " | 2.2 | 2.5 |
| Sulfolane, Neodecanoic acid | " | " | 1.5 | 1.6 |
| Sulfolane, m-Nitrobenzoic acid | " | " | 1.1 | 1.4 |
| Sulfolane, Octanoic acid | " | " | 1.9 | 1.8 |
| Sulfolane, Pelargonic acid | " | " | 1.6 | 1.2 |
| Sulfolane, Salicylic acid | " | " | 1.2 | 1.3 |
| Sulfolane, Sebacic acid | " | " | 2.7 | 1.7 |
| Sulfolane, Thiosalicylic acid | " | " | 5.5 | 4.1 |
| Sulfolane, m-Toluic acid | " | " | 2.3 | 1.7 |
| Sulfolane, Azelaic acid, Ethylene glycol diacetate | (½)[3] | (2/5)[3] | 1.6 | 2.1 |
| Sulfolane, Adipic acid, Benzyl ether | " | " | 1.6 | 1.9 |
| Sulfolane, Benzoic acid, Dipropylene glycol dibenzoate | " | " | 1. | 1.2 |
| Sulfolane, Cinnamic acid, 2-Methoxyethyl ether | " | " | 2.1 | 2.6 |
| Sulfolane, Decanoic acid, Acetophenone | " | " | 1.1 | 1.5 |
| Sulfolane, Glutaric acid, Methyl isoamyl ketone | " | " | 1.3 | 1.9 |
| Sulfolane, Itaconic acid, Glycerol triacetate | " | " | 2.9 | 2.5 |
| Sulfolane, Maiic acid, Ethylene glycol butyl ether acetate | " | " | 1.8 | 1.3 |
| Sulfolane, Octanoic acid, Isophorone | " | " | 2.2 | 1.5 |
| Sulfolane, Salicylic acid, Cyclopentanone | " | " | 1.2 | 1.2 |
| Sulfolane, Sebacic acid, Nitrobenzene | " | " | 1.6 | 1.3 |
| Sulfolane, Thiosalicylic acid, Diethyl maleate | " | " | 2.1 | 1.3 |

TABLE 3

Potential Agents Containing Sulfolane Which Are Ineffective

Compounds

Sulfolane, Acetyl salicylic acid, Benzyl acetate
Sulfonane, p-tert. Butyl benzoic acid, Diethylene glycol diethyl ether
Sulfonane, Heptanoic acic, Benzyl benzoate
Sulfonane, Hexanoic acid, Ethyl benzoate
Sulfonane, Myristic acid, Isobutyl heptyl ketone
Sulfonane, Neodecanoic acid, Methyl salicylate
Sulfonane, m-Nitrobenzoc acid, Dipropylene glycol methyl ether acetate
Sulfonane, Pelargonic acid, 2-Undecanone
Sulfonane, o-Toluic acid, Propropnenone
Sulfonane, m-Toluic acid, Butyl ether
Sulfonane, p-Toluic acid, Hexyl acetate

TABLE 4

Effective Extractive Distillation Agents For 4-Methy-2-pentanone From Acetic Acid

| Compounds | Ratios | | Relative Volatilities | |
|---|---|---|---|---|
| Sulfolane | 2 | 12/5 | 1.7 | 2.7 |
| Sulfolane, Adipic acid | (½)[2] | (3/5)[2] | 1.2 | 2.5 |
| Sulfolane, Acetyl salicylic acid | " | " | 1.2 | 2.0 |
| Sulfolane, Azelaic acid | " | " | 2.1 | 1.2 |

TABLE 4-continued

Effective Extractive Distillation Agents For 4-Methy-2-pentanone From Acetic Acid

| Compounds | Ratios | | Relative Volatilities | |
|---|---|---|---|---|
| Sulfolane, Benzoic acid | " | " | 1.8 | 1.5 |
| Sulfolane, p-tert. Butyl benzoic acid | " | " | 3.8 | 2.0 |
| Sulfolane, Cinnamic acid | " | " | 1.5 | 1.2 |
| Sulfolane, Decanoic acid | " | " | 1.7 | 1.2 |
| Sulfolane, Glutaric acid | " | " | 1.7 | 1.5 |
| Sulfolane, Heptanoic acid | " | " | 1.4 | 1.7 |
| Sulfolane, Hexanoic acid | " | " | 1.3 | 2.8 |
| Sulfolane, Hexahydro phthalic acid | " | " | 2.8 | 1.5 |
| Sulfolane, Itaconic acid | " | " | 2.3 | 1.5 |
| Sulfolane, Myristic acid | " | " | 1.8 | 1.4 |
| Sulfolane, Neodecanoic acid | " | " | 1.4 | 1.7 |
| Sulfolane, Octanoic acid | " | " | 1.2 | 1.3 |
| Sulfolane, Pelargonic acid | " | " | 2.4 | 1.2 |
| Sulfolane, Salicylic acid | " | " | 1.4 | 1.4 |
| Sulfolane, Sebacic acid | " | " | 1.5 | 1.2 |
| Sulfolane, Tetrahydro phthalic acid | " | " | 1.5 | 1.4 |
| Sulfolane, Thiosalicylic acid | " | " | 2.1 | 1.6 |
| Sulfolane, o-Toluic acid | " | " | 2.9 | 1.2 |
| Sulfolane, m-Toluic acid | " | " | 1.7 | 1.3 |
| Sulfolane, p-Toluic acid | " | " | 1.5 | 1.3 |
| Sulfolane, Undecanoic acid | " | " | 1.9 | 1.2 |
| Sulfolane, Adipic acid, Anisole | $(\frac{1}{3})^3$ | $(2/5)^3$ | 1.8 | 1.2 |
| Sulfolane, Acetyl salicyic acid, Methyl salicylate | " | " | 1.4 | 1.6 |
| Sulfolane, Azelaic acid, Ethylene glycol ether | " | " | 1.4 | 1.3 |
| Sulfolane, p-tert. Butyl benzoic acid, Isobornyl acetate | " | " | 1.4 | 3.3 |
| Sulfolane, Cinnamic acid, n-Butyl ether | " | " | 1.8 | 1.3 |
| Sulfolane, Decanoic acid, Adiponitrile | " | " | 2.5 | 1.5 |
| Sulfolane, Glutaric acid, Propiophenone | " | " | 2.3 | 1.3 |
| Sulfolane, Heptanoic acid, Butyl benzoate | " | " | 2.9 | 2.5 |
| Sulfolane, Hexahydro phthalic acid, Methyl benzoate | " | " | 1.4 | 1.5 |
| Sulfolane, Itaconic acid, Ethyl salicylate | " | " | 1.4 | 1.8 |
| Sulfolane, Neodecanoic acid, Benzyl acetate | " | " | 1.6 | 1.2 |
| Sulfolane, Octanoic acid, Cyclohexanone | " | " | 3.1 | 2.7 |
| Sulfolane, Pelargonic acid, 2-Octanone | " | " | 1.2 | 2.2 |
| Sulfolane, Salicylic acid, Phenyl acetate | " | " | 1.5 | 1.4 |
| Sulfolane, Sebacic acid, 2-Heptanone | " | " | 3.0 | 1.8 |
| Sulfolane, Tetrahydro phthalic acid, Dipropylene glycol methyl ether | " | " | 1.5 | 2.6 |
| Sulfolane, Thiosalicylic acid, Diethylene glycol diethyl ether | " | " | 1.7 | 1.3 |
| Sulfolane, o-Toluic acid, 2-Methoxyethyl ether | " | " | 1.6 | 2.3 |
| Sulfolane, p-Toluic acid, Ethyl phenyl acetate | " | " | 1.4 | 1.2 |

TABLE 5

Potential Extractive Distillation Agents Containing Sulfolane Which Are Ineffective For 4-Methyl-2-pentanone from Acetic Acid Sulfolane, Benzoic acid, Diethylene glycol dibenzoate
Sulfolane, Hexanoic acid, Methyl benzoate
Sulfolane, Myristic acid, Isobutyl neptyl ketone
Sulfolane, m-Toluic acid, Ethylene glycol methyl ether acetate
Sulfolane, Undecanoic acid, Benzonitrile

TABLE 6

Data From Runs Made In Recrification Column

| Agent | Column | Time, hrs. | Weight % Ketone | Weight % Formic acid | Relative Volatility |
|---|---|---|---|---|---|
| 50% Sulfolane, | Overhead | 0.5 | 40 | 60 | 1.69 |
| 50% Heptanoic acid | Bottoms | | 4.2 | 95.8 | |
| 50% Sulfolane, | Overhead | 1.5 | 48.1 | 51.9 | 1.86 |
| 50% Heptanoic acid | Bottoms | | 3.5 | 96.5 | |

| Agent | Column | Time, hrs. | Weight % Ketone | Weight % Acetic acid | Relative Volatility |
|---|---|---|---|---|---|
| 33% Sulfolane, 33% Heptanoic acid 33% Methyl benzoate | Overhead | 0.5 | 69.2 | 30.8 | 1.74 |
| | Bottoms | | 10.3 | 89.7 | |
| 33% Sulfolane, 33% Heptanoic acid 33% Methyl benzoate | Overhead | 1.3 | 73.3 | 26.7 | 2.04 |
| | Bottoms | | 6.7 | 93.3 | |

One third part of sulfolane plus ⅓ part of cinnamic acid plus ⅓ part of 2-methoxyethyl ether with one part of the 4-methyl-2-pentanone-formic acid mixture gives a relative volatility of 2.1, with 2/5 parts, these three give a relative volatility of 2.6. In every example in Table 2, the starting material is a 4-methyl-2-pentanone-formic acid mixture which possesses a relative volatility of about 1.3.

One of the mixtures, sulfolane and heptanoic acid, listed in Table 2 and whose relative volatility had been determined in the vapor-liquid equilibrium still, was then evaluated in a glass perforated plate rectification column possessing 5.3 theoretical plates and the results listed in Table 6. The data in Table 6 was obtained in the following manner. The charge was 200 grams of 50% 4-methyl-2-pentanone 50% formic acid and after a half hour of operation in the 5.3 theoretical plate column to establish equilibrium, a mixture containing 50% sulfolane, 50% heptanoic acid at 85° C. and 20 ml/min. was pumped in. The rectification was continued with sampling of overhead and bottoms after a half hour. The analysis is shown in Table 6 and was 40% 4-methyl-2-pentanone, 60% formic acid in the overhead and 4.2% 4-methyl-2-pentanone, 95.8% formic acid in the bottoms which gives a relative volatility of 1.69 of 4-methyl-2-pentanone to formic acid. After 1.5 hours of continuous operation, the overhead was 48.1% 4-methyl-2-pentanone, 51.9 formic acid, the bottoms was 3.5% 4-methyl-2-pentanone, 96.5% formic acid which is a relative volatility of 1.86.

Table 3 contains several potential extractive distillation agents which might be expected to be successful but which proved to be ineffective in the separation of 4-methyl-2-pentanone from formic acid.

Table 4 lists sulfolane and its mixtures that we have found to be effective in separating 4-methyl-2-pentanone from acetic acid. The compounds which are effective are adipic acid, acetyl salicylic acid, azelaic acid, benzoic acid, p-tert. butyl benzoic acid, cinnamic acid, decanoic acid, glutaric acid, heptanoic acid, hexanoic acid, hexahydro phthalic acid, itaconic acid, myristic acid, neodecanoic acid, octanoic acid, pelargonic acid, salicylic acid, sebacic acid, tetrahydro phthalic acid, thiosalicylic acid, o-toluic acid, m-toluic acid, p-toluic acid, undecanoic acid, anisole, methyl salicylate, ethylene glycol phenyl ether, isobornyl acetate, n-butyl ether, adiponitrile, propiophenone, butyl benzoate, methyl benzoate, ethyl salicylate, benzyl acetate, cyclohexanone, 2-octanone, phenyl acetate, 2-heptanone, dipropylene glycol methyl ether, diethylene glycol diethyl ether, 2-methoxyethyl ether and ethyl phenyl acetate.

THE USEFULNESS OF THE INVENTION

The usefulness or utility of this invention can be demonstrated by referring to the data presented in Tables 1-6. All of the successful extractive distillation agents show that 4-methyl-2-pentanone can be separated from formic acid or acetic acid by means of distillation in a rectification column and that the ease of separation as measured by relative volatility is considerable. Without these extractive distillation agents, little improvement will occur in the rectification column. The data also show that the most attractive agents will operate at a boilup rate low enough to make this a useful and efficient method of recovering high purity 4-methyl-2-pentanone from any mixture with acetic or formic acids. The stability of the compounds used and the boiling point difference is such that complete recovery and recycle is obtainable by a simple distillation and the amount required for makeup is small.

WORKING EXAMPLES

Example 1

Forty grams of 4-methyl-2-pentanone-acetic acid mixture and 50 grams of sulfolane were charged to a vapor-liquid equilibrium still and refluxed for 12 hours. Analysis indicated a vapor composition of 25% 4-methyl-2-pentanone, 75% acetic acid, a liquid composition of 16.4% 4-methyl-2-pentanone, 83.6% acetic acid which is a relative volatility of 1.7. Ten grams of sulfolane were added and refluxing continued for another eight hours. Analysis indicated a vapor composition of 33.3% 4-methyl-2-pentanone, 66.7% acetic acid and a liquid composition of 15.4% 4-methyl-2-pentanone, 84.6% acetic acid which is a relative volatility of 2.7.

Example 2

Eighty grams of a 4-methyl-2-pentanone-acetic acid mixture, 25 grams of sulfolane and 25 grams of heptanoic acid were charged to the vapor-liquid equilibrium still and refluxed for 16 hours. Analysis indicated a vapor composition of 21.6% 4-methyl-2-pentanone, 78.4% acetic acid, a liquid composition of 16.4% 4-methyl-2-pentanone, 83.6% acetic acid which is a relative volatility of 1.4. Five grams of sulfolane and five grams of heptanoic acid were added and refluxing continued for another 12 hours. Analysis indicated a vapor composition of 18.5% 4-methyl-2-pentanone, 81.5% acetic acid, a liquid composition of 11.8% 4-methyl-2-pentanone, 89.2% acetic acid which is a relative volatility of 1.7.

Example 3

Fifty grams of a 4-methyl-2-pentanone-formic acid mixture, 17 grams of sufolane, 17 grams of azelaic acid and 17 grams of ethylene glycol diacetate were charged to the vapor-liquid equilibrium still and refluxed for 16 hours. Analysis indicated a vapor composition of 21.1% 4-methyl-2-pentanone, 78.9% formic acid, a liquid composition of 14.5% 4-methyl-2-pentanone, 85.5% formic acid which is a relative volatility of 1.6. Three grams each of sulfolane, azelaic acid and ethylene glycol diacetate were added and refluxing continued for another eight hours. Analysis indicated a vapor composition of 19.1% 4-methyl-2-pentanone, 80.9% formic acid, a liquid composition of 10% 4-methyl-2-pentanone, 90% formic acid which is a relative volatility of 2.1.

Example 4

A glass perforated plate rectification column was calibrated with ethylbenzene and p-xylene which possesses a relative volatility of 1.06 and found to have 5.3 theoretical plates. A solution comprising 100 grams of 4-methyl-2-pentanone and 100 grams of formic acid was placed in the stillpot and heated. When refluxing began, an extractive agent comprising 50% sulfolane and 50% heptanoic acid was pumped into the column at a rate of 16 ml/min. The temperature of the extractive agent as it entered the column was 90° C. After establishing the feed rate of the extractive agent, the heat input to the 4-methyl-2-pentanone and formic acid in the stillpot was adjusted to give a total reflux rate of 10–20 ml/min. After one half hour of operation, the overhead and bottoms samples of approximately two ml. were collected and analysed by gas chromatography. The overhead analysis was 40% 4-methyl-2-pentanone, 60% formic acid and the bottoms analysis was 4.2% 4-methyl-2-pentanone, 95.8% formic acid. Using these compositions in the Fenske equation, with the number of theoretical plates in the column being 5.3, gave an average relative volatility of 1.69 for each theoretical plate. After 1.5 hours of total operating time, the overhead and bottoms samples were again taken and analysed. The overhead composition was 48.1% 4-methyl-2-pentanone, 51.9% formic acid and the bottoms composition was 3.5% 4-methyl-2-pentanone, 96.5% formic acid. This gave an average relative volatility of 1.86 for each theoretical plate. These data are presented in Table 6.

We claim:

1. A method for recovering 4-methyl-2-pentanone from mixtures of 4-methyl-2-pentanone and formic acid which comprises distilling a mixture of 4-methyl-2-pentanone and formic acid in a rectification column in the presence of about one part of an extractive agent per part of the 4-methyl-2-pentanone-formic acid mixture, recovering 4-methyl-2-pentanone as overhead product and obtaining the extractive agent and the formic acid from the stillpot, wherein said extractive agent comprises sulfolane.

2. The method of claim 1 in which the extractive agent comprises sulfolane and at least one material selected from the group consisting of adipic acid, acetyl salicylic acid, azelaic acid, benzoic acid, p-tertiary butyl benzoic acid, cinnamic acid, decanoic acid, glutaric acid, heptanoic acid, hexanoic acid, itaconic acid, malic acid, neodecanoic acid, m-nitrobenzoic acid, octanoic acid, pelargonic acid, salicylic acid, sebacic acid, thiosalicylic acid, m-toluic acid, ethylene glycol diacetate, benzyl ether, dipropylene glycol dibenzoate, 2-methoxyethyl ether, acetophenone, methyl isoamyl ketone, glycerol triacetate, ethylene glycol butyl ether acetate, isophorone, cyclopentanone, nitrobenzene and diethyl maleate.

3. A method for recovering 4-methyl-2-pentanone from mixtures of 4-methyl-2-pentanone and acetic acid which comprises distilling a mixture of 4-methyl-2-pentanone and acetic acid in a rectification column in the presence of about one part of an extractive agent per part of the 4-methyl-2-pentanone-acetic acid mixture, recovering 4-methyl-2-pentanone as overhead product and obtaining the extractive agent and the acetic acid from the stillpot, wherein said extractive agent comprises sulfolane.

4. The method of claim 3 in which the extractive agent comprises sulfolane and at least one material selected from the group consisting of adipic acid, acetyl salicylic acid, azelaic acid, benzoic acid, p-tertiary butyl benzoic acid, cinnamic acid, decanoic acid, glutaric acid, heptanoic acid, hexanoic acid, hexahydro phthalic acid, itaconic acid, myristic acid, neodecanoic acid, octanoic acid, pelargonic acid, salicylic acid, sebacic acid, tetrahydrophthalic acid, thiosalicylic acid, o-toluic acid, m-toluic acid, p-toluic acid, undecanoic acid, anisole, methyl salicylate, ethylene glycol phenyl ether, isobornyl acetate, n-butyl ether, adiponitrile, propiophenone, butyl benzoate, methyl benzoate, ethyl salicylate, benzyl acetate, cyclohexanone, 2-octanone, phenyl acetate, 2-heptanone, dipropylene glycol methyl ether, diethylene glycol diethyl ether, 2-methoxyethyl ether and ethyl phenyl acetate.

* * * * *